(12) United States Patent
Grassi Osma et al.

(10) Patent No.: US 9,295,578 B2
(45) Date of Patent: Mar. 29, 2016

(54) FASTENING DEVICE FOR PEOPLE WITH REDUCED MOBILITY CONDITIONS

(71) Applicant: CORPORACIÓ SANITARIA PARC TAULI, Sabadell (ES)

(72) Inventors: Carlos Grassi Osma, Sant Just Desvern (ES); Luis Capella Folguera, La Garriga (ES); Laura Vidaña Moya, Terrassa (ES); Beatriz Robles Moreno, Sabadell (ES); Eva Maria Carrasco Rilova, Sabadell (ES); Maria Victoria Marti Del Peral, Sabadell (ES)

(73) Assignee: CORPORACIO SANITARIA PARC TAULI, Sabadell (ES)

( * ) Notice: Subject to any disclaimer, the term of this patent is extended or adjusted under 35 U.S.C. 154(b) by 0 days.

(21) Appl. No.: 14/419,155

(22) PCT Filed: Jul. 30, 2013

(86) PCT No.: PCT/EP2013/066010
§ 371 (c)(1),
(2) Date: Feb. 2, 2015

(87) PCT Pub. No.: WO2014/020028
PCT Pub. Date: Feb. 6, 2014

(65) Prior Publication Data
US 2015/0157489 A1    Jun. 11, 2015

(30) Foreign Application Priority Data

Aug. 3, 2012    (ES) .................................. 201231269

(51) Int. Cl.
*A47D 15/00*    (2006.01)
*A61F 5/37*    (2006.01)
(Continued)

(52) U.S. Cl.
CPC ................ *A61F 5/3792* (2013.01); *A61G 5/10* (2013.01); *A62B 35/00* (2013.01)

(58) Field of Classification Search
CPC .... A47D 15/006; B60R 22/00; B60R 22/105; B60N 2/2812; B60N 2/2839
USPC ......... 297/464, 467, 468, 474, 475, 481, 484, 297/485, 487
See application file for complete search history.

(56) References Cited

U.S. PATENT DOCUMENTS 3,301,594 A * 1/1967 Pukish, Jr. .................... 297/467
3,604,750 A * 9/1971 Doering ........................ 297/467
(Continued)

FOREIGN PATENT DOCUMENTS

EP    1666014 A2    6/2006
ES    1073787        2/2011

*Primary Examiner* — Laurie Cranmer
(74) *Attorney, Agent, or Firm* — Lucas & Mercanti, LLP (57) ABSTRACT

Fastening device for people with reduced mobility conditions, of the variety employed in chairs or arm chairs in domestic, geriatric, care or hospital environments, comprising fixation means (50), which can be adapted to the back of the chair or arm chair and containing means (100) to contain the person to be fastened. Said device (1) comprises a portable support body (10) in which said fixation means (50) and containing means (100) are located and the containing means (100) comprise at least one containing strap (101, 102, 103) connected to an emergency locking retractor (104, 105, 106) which is configured in order to facilitate the free movement of the person fastened to said chair or arm chair and to prevent falling movement of the same.

13 Claims, 8 Drawing Sheets

(51) Int. Cl.
*A61G 5/10* (2006.01)
*A62B 35/00* (2006.01)

(56) References Cited

U.S. PATENT DOCUMENTS

| | | | |
|---|---|---|---|
| 3,612,605 A * | 10/1971 | Posey, Jr. | 297/484 |
| 5,215,354 A * | 6/1993 | Grene | 297/485 |
| 5,439,253 A | 8/1995 | Trubiano | |
| 5,496,092 A * | 3/1996 | Williams et al. | 297/250.1 |
| 5,628,548 A * | 5/1997 | Lacoste | 297/484 |
| 6,082,826 A | 7/2000 | Moreno | |
| 6,402,251 B1 * | 6/2002 | Stoll | 297/485 |
| 6,547,334 B1 * | 4/2003 | Girardin | 297/484 |
| 6,616,242 B1 * | 9/2003 | Stoll | 297/485 |
| 6,631,959 B1 * | 10/2003 | Amondo et al. | 297/485 |
| 6,688,701 B1 * | 2/2004 | Weaver | 297/485 |
| 7,347,494 B2 * | 3/2008 | Boyle et al. | 297/253 |
| 8,794,709 B2 * | 8/2014 | Kennedy | 297/485 |
| 2002/0000747 A1 * | 1/2002 | Hee | 297/484 |
| 2007/0052278 A1 * | 3/2007 | Jones | 297/485 |
| 2011/0049962 A1 | 3/2011 | Sonnendorfer et al. | |

* cited by examiner

FASTENING DEVICE FOR PEOPLE WITH REDUCED MOBILITY CONDITIONS

CROSS REFERENCE TO RELATED APPLICATION

This Application is a 371 of PCT/EP2013/066010 filed on Jul. 30, 2013 which, in turn, claimed the priority of Spanish Patent Application No. P201231269 filed on Aug. 3, 2012, both applications are incorporated herein by reference.

OBJECT OF THE INVENTION

The present invention refers to a fastening device for people with reduced mobility conditions, of the variety used on chairs or armchairs in domestic, geriatric, care or hospital environments or in any other environment in general.

The device object of the present invention has been especially designed to guarantee the safety of the people fastened to the same, as well as to increase their level of comfort and freedom of movement. In turn, said device improves the adaptability benefits in order to be fixed to any type of chair or arm chair and facilitates the manipulation of the same in relation to existing fastening devices.

BACKGROUND OF THE INVENTION

At present, fastening devices for people with reduced mobility conditions are known, which are of the abovementioned variety and which facilitate adequate fastening of the person to be fastened, hereinafter the user, to a greater or lesser degree, as well as facilitating a more or less secure fixing to a certain variety of chairs and/or arm chairs.

For example, document ES1073787 demonstrates a simple fastening device, the entirety of which is formed by a set of flexible straps, each one of which performs a certain function. In this sense, a first strap is responsible for fixing the device to a chair or arm chair, holding the back of the same, whilst a second strap does the same to the seat of said chair or arm chair. A third strap is responsible for containing the thoracic area of the user. Said third strap is "V" shaped, the two upper ends of which are joined to the first strap, whilst its lower vertex passes through a ring made of flexible strap material. The latter is responsible for containing the inguinal area of the user and is in turn crossed by a second strap. All of the straps are joined together by means of employing quick opening and closing systems of the Velcro® variety.

This kind of device has many limitations, which are mainly related to the lack of user safety, the user feeling uncomfortable and the difficulties encountered when users' assistants are manipulating the device.

As far as the lack of safety is concerned, it is worth pointing out that the quick opening and closing systems do not always resist when the user eventually falls, for example when they show signs of prolonged wear or in the event of the device being mounted incorrectly. It is also possible that the user himself works easily on the many straps and frees himself from them. Finally, fixing using this kind of system is not always effective and does not always adapt to a large range of chairs or arm chairs.

As far as user discomfort is concerned, the high amount of pressure exerted on the inguinal area of the user has been identified as a source of discomfort, bearing in mind that the vertex of the thoracic containing strap and the inguinal containing ring are concentrated in a very small area, which gives rise to significant discomfort. Other reasons may be added to this, owing to the fact that the strap used to fix the seat is located below the users' legs. Finally, the users' freedom of movement is very restricted, unless freedom of movement is achieved at the risk of their safety, not tightening the thoracic containing strap too tightly.

Finally, various aspects are highlighted as far as manipulating the device is concerned. Generally, any mounting based exclusively on the separate arrangement of a set of independent straps usually generates problems and on many occasions, results in the device being mounted incorrectly. Meanwhile, a device with a notable number of separate components is more bothersome when it comes to collecting and transporting it, in addition to the fact that the risk of losing one of the components is increased.

Document U.S. Pat. No. 5,439,253 relates to an automatically retractable safety belt device for fastening a child seated in a seat compartment of a shopping cart. This device is provided with containing straps which are connected to simple springs or springs retractors. The springs are configured to exert a variable restraining force, which depends on the extension of the springs. When the springs are totally extended, a maximum pulling force over the child is applied. As the springs cannot be extended further, the device does not allow a smooth removal of the containing strap. When the springs are partially extended, a partial pulling force over the child is applied. As the springs can be extended further, the device does not lock instantly the removal of the containing strap when a brusque movement from said child is detected. Therefore, the springs or spring retractors do not allow a smooth removal of the containing strap, once the same has been adjusted to the child fastened to the seat compartment, and at the same time an instant locking of said removal when a brusque movement from said child is detected.

The present invention resolves the problems set out above in a fully satisfactory way, owing to a fastening device which guarantees the safety of its uses, increasing their level of comfort and freedom of movement. At the same time, it has greater adaptability benefits in that it can be fixed to any kind of chair or arm chair and facilitates the manipulation of the same, in comparison to existing fastening devices.

DESCRIPTION OF THE INVENTION

The fastening device for people with reduced mobility conditions, object of the present invention, of the abovementioned variety, comprises adaptable fixation means, which adapt to the back of the chair or arm chair and containing means provided with at least one containing strap to contain the person to be fastened.

The device comprises a portable support body, in which said fixation and containing means are arranged. The device is characterised in that the containing strap is connected to an emergency locking retractor, which is configured to facilitate the free movement of the person fastened to said chair or arm chair and to prevent the same from falling by preventing falling movements.

In the first instance, the support body serves to house the various components which form part of the device, guaranteeing that it is fixed, deployed and adjusted correctly. In the second instance, the support body also serves to facilitate the transportation and manipulation of the device. The support body preferably consists of a bag or rucksack made of textile fabric, to which other reinforcement materials may be added in order to facilitate the correct operation thereof. In accordance with other embodiments, the support body may be formed by a box, case or any other kind of rigid or semi-rigid shell in general.

The support body comprises:
- a support base, arranged on the inside of said support body, upon which the fixation and containing means are supported and;
- a plurality of openings which extend said means and facilitate the manipulation of the same.

The support base may be formed in several ways. For example, in flexible support bodies, of the bag or rucksack variety, the support base may consist of a metal plate which is duly lined or joined by other means, to the bag or rucksack. In rigid or semi-rigid support bodies, of the case or shell variety, the support base may simply consist of an internal surface within the same.

In order to facilitate both the transportation of the device and the manipulation and maintenance of the same, the support body comprises:
- a quick opening and closing element which grants access to the fixation and containing means and;
- a transportation element, which facilitates the transportability of the support body.

The opening and closing elements for flexible support bodies may consist of all kinds of zips, buttons, clasps, snap fasteners or quick fastening elements of the Velcro® variety, amongst others, with which one or more compartments in which the fixation and containing means can be accessed. For rigid or semi-rigid support bodies, the opening and closing elements may consist of lids, removable covers or widows, which facilitate access to said compartments. The transportation elements are preferably formed by handles, carrying straps, straps or belts, etc.

The fixation means are those means which make it possible to fix the fastening device to the chair or arm chair. The fixation means comprise:
- an automatic locking retractor;
- a fastening strap with an internal end connected to the automatic locking retractor and an external end, which has a clasp mechanism and;
- a retaining mechanism, which is configured to retain the clasp mechanism and has an unclasping mechanism in order to free the same.

The automatic locking retractor, also known as ALR, is configured to prevent the fixation strap from being removed once the same has been adjusted to the back of the chair or arm chair. In this way, the fastening strap remains well adjusted to the back at all times, thus preventing the same from becoming loose and as a result, preventing the device from becoming detached. An automatic locking retractor usually operates by completely removing the strap from the same, which is when a locking mechanism is activated. From this moment on, the automatic locking retractor only allows the strap to be rewound but not to be removed. Removing the strap once again requires the strap to be completely rewound in order to deactivate the locking mechanism. Said mechanism may in some cases be arranged at various intermediate points along the length of the strap, operating in the same way. This prevents having to remove the strap too much when the device is attached to chairs or arm chairs which are not very wide.

The clasp mechanism is preferably configured by a metal buckle or tongue, which is retained by a retaining mechanism configured as a female connector, whilst the unclasping mechanism consists of a button, which makes it possible to disengage the connector tongue. Said button is located beyond the users' reach or at a point which is difficult to access, in order to prevent said user from operating the same and causing unwanted release from the fastening device.

With the aim of providing additional fastening, the fixation means additionally comprise:
- an elastic energy storage element arranged between the fixation strap and the clasp mechanism and;
- a manual tensioning element, which makes it possible to roll the fixation strap in the automatic locking device, in order to tense the energy storage.

In other words, once the fixation strap has been adjusted, it is possible to roll a little more, operating on the manual tensioning element. In this case, the energy storage tenses but cannot free said energy, because the automatic locking retractor does not allow more strap to be removed. This prevents the strap from becoming loose even more and as a result, ensures that the device has been fixed to the chair or arm chair correctly. The energy storage is preferably consists of a rubber made of plastic material, which is robust enough to be able to prevent unwanted breakages.

The containing means are those means which make it possible to fasten the user in a safe and comfortable way. These means comprise:
- a first emergency locking retractor, oriented towards a first side of the support body and;
- a first containing strap with one internal end connected to the first automatic emergency retractor and an external end which has a first clasping element.

The first containing strap is configured to be fastened to the user, facilitating the free movement of the same and preventing accidental falling movements, owing to the action of the first emergency locking retractor.

Of the various possible fastening formations, the containing means preferably and additionally comprise the following:
- a second emergency locking retractor, orientated towards a second side of the support body, facing the first side and;
- a second containing strap with an internal end, which is connected to the second emergency locking retractor and an external end, which has a second clasp element.

In this way, the first and second containing straps stem from opposing sides of the chair or arm chair in order to hold the user in an equidistant manner in their abdominal area, in the form of a belt.

The containing means preferably comprise:
- a third emergency locking retractor, orientated towards a third side of the support body and;
- a third containing strap with an internal end, which is connected to a third emergency locking retractor and with an external end, which has a third clasp element.

The third side of the support body corresponds to a lower side of the same, arranged between the first and second side, in such a way that the third containing strap is oriented towards the seat of the chair or arm chair. Likewise, the containing means comprise a flexible containing pad which has:
- an abdominal piece and;
- an inguinal piece, which extends perpendicularly from said abdominal piece.

The abdominal piece comprises at least one lateral anchoring element, configured to anchor the first or second clasp element. The abdominal piece preferably comprises two lateral anchoring elements, one for the first containing strap and the other for the second containing strap.

The inguinal piece comprises at least one lower anchoring element, configured to anchor the third clasp element.

The containing pad is preferably made of washable textile material and as far as possible, is free of rigid, loose or semi-loose pieces, made of plastic or metal materials, which make the same difficult to wash. In this sense, the lateral anchoring elements are configured by means of pockets formed on the pad itself, which work alongside a first and second clasp element in the form of a hook. Meanwhile, the lower anchoring element is configured by a hoop of textile material, also formed on the pad itself, upon which the third clasp element may be tethered.

The emergency locking retractors mentioned above, also known as ELRs, are configured in order to facilitate the smooth removal of the containing strap, once the same has been adjusted to the user, at the same time instantly locking said removal when a brusque movement from said user is detected. This facilitates the free and controlled movement of the person fastened to said chair or arm chair, whilst also preventing falling movements of the same. This is mainly achieved by means of employing an inertia reel, which is sensitive to the movement of the container strap. The inertia reel is joined to the container strap and acts as a bobbin of the same. A spring makes it possible to apply rotational force to the inertia reel, in order to rewind the strap when it is loose and keep it collected. The inertia reel blocks the container strap in order to prevent it from being removed, by means of a centrifuge locking mechanism, the activation of which depends on the speed at which the reel rotates as the strap is removed.

According to a first fastening option, the user remains seated on the chair or arm chair, fastened in the abdominal and inguinal areas, being able to move freely and in a controlled manner in these areas, whilst also being protected from an eventual fall.

Nevertheless, for users with more critical mobility conditions, it may be necessary to impede the free movement of the abdominal area and/or the inguinal area. For this reason, some or all of the emergency locking retractors comprise a manual locker, configured to impede the free movement of the person fastened to said chair or arm chair. Said manual locker disables the smooth removal of the container straps, once adjusted to the user.

In addition, the fastening device for people with reduced mobility conditions, object of the present invention, comprises at least one thoracic fastening strap, configured to be joined to the containing pad and to the support body. For this reason, the abdominal piece comprises at least one upper anchoring element, configured to anchor a first end of the fastening strap, whilst the support body comprises as least one external anchoring element, configured to anchor a second end of the fastening strap. The device preferably comprises two thoracic fastening straps.

The thoracic fastening straps are made of washable textile material and as far as possible, are free of rigid, loose or semi-loose pieces made of plastic or metal materials, which make it difficult to wash the same. In this sense, the upper anchoring elements are configured by means of bands of textile material made up on the pad itself, which work alongside the first ends of the fastening straps. Meanwhile, both the first end and the second end of the fastening strap are formed by quick opening and closing systems of the velcro® variety, which can be easily washed and may be joined and/or tethered to the bands of the pad and to the anchoring elements external to the support body.

According to this second fastening option, the user remains seated on the chair or arm chair, fastened at their abdominal, inguinal or thoracic area, having free and controlled movement of said areas whilst also being protected against an eventual fall.

For users with more critical mobility conditions, it may be necessary to impede the free movement of the thoracic area, carrying out the method described above for the abdominal and inguinal areas.

BRIEF DESCRIPTION OF THE DRAWINGS

Below is a brief description of a series of drawings which facilitate a better understanding of the invention and relate specifically to one preferred embodiment of said invention, providing a non-limiting example of the same.

PREFERRED EMBODIMENT OF THE INVENTION

Figure 1:
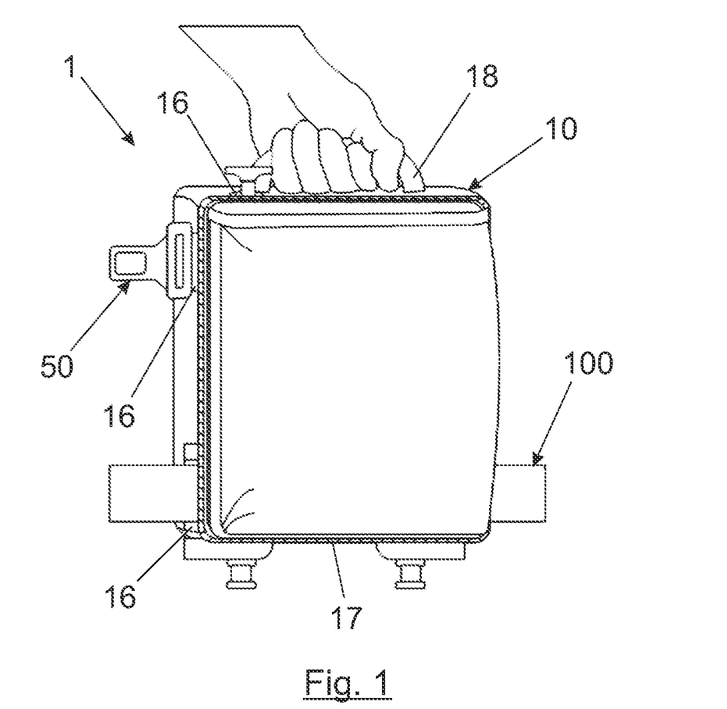
FIG. 1 is a perspective representation of the fastening device, object of the present invention, in its collected position.

FIG. 1 is a perspective representation of the fastening device, object of the present invention, in its collected position. As can be seen, the fastening device (1) comprises fixation means (50), which can be adapted to the back of a chair or arm chair and containing means (100) to contain the person to be fastened, arranged on a portable support body (10).

Figure 2:
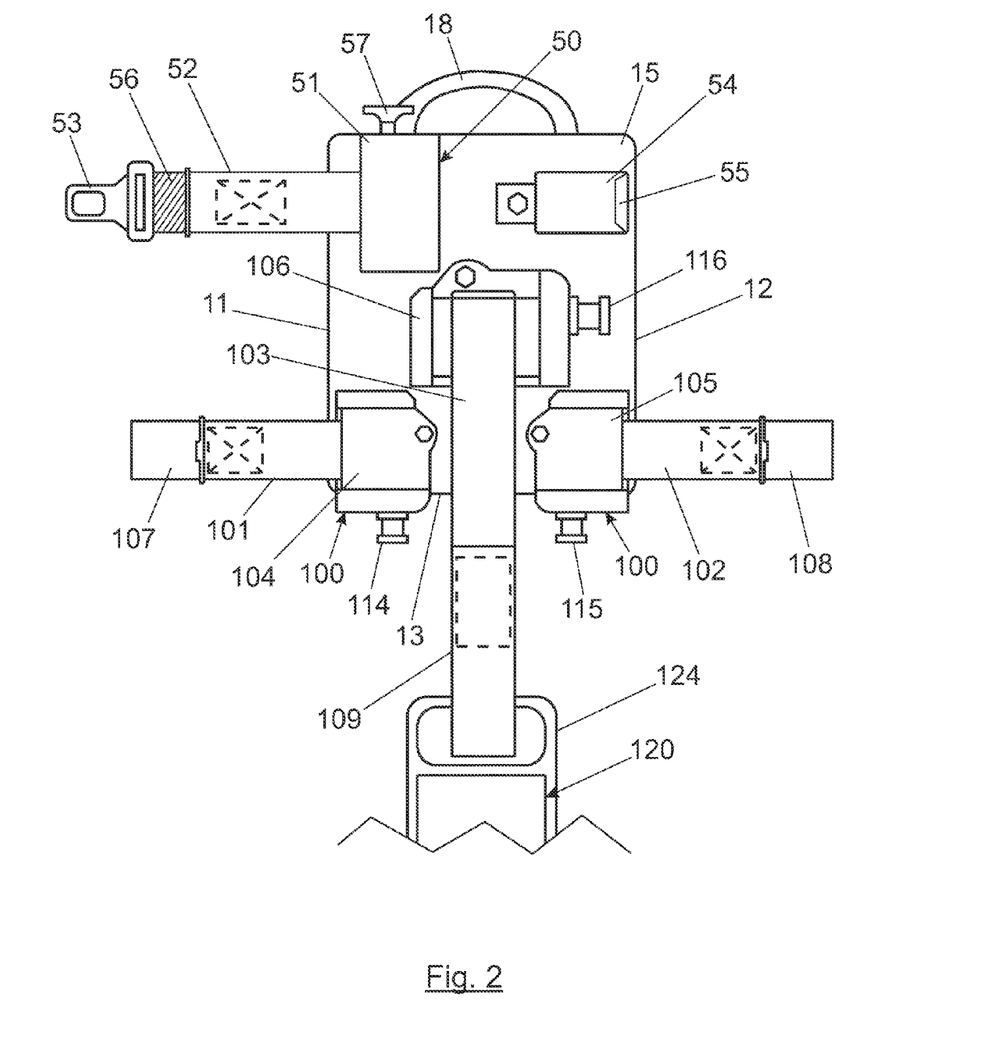
FIG. 2 is an elevation view of the internal part of the fastening device.

FIG. 2 is an elevation view of the internal part of the fastening device. As can be seen, the containing means (100) comprise at least three containing straps (101, 102, 103), each one of which is connected to an emergency locking retractor (104, 105, 106), which is configured in order to facilitate the free movement of the person fastened to said chair or arm chair and in order to prevent falling movements of the same.

In the present example, the support body (10) consists of a bag or rucksack made of textile fabric. The support body (10) comprises:
  a support base (15), arranged inside said support body (10), upon which the fixation (50) and containing (100) means are supported and;
  a plurality of openings (16) (see FIG. 1), which extend said means (50, 100) and facilitate the manipulation thereof.

In the present example, the support base (15) consists of a rectangular metal plate, duly joined to the bag or rucksack.

In order to facilitate both the transportation of the device (1) and the manipulation and maintenance thereof, the support body (10) comprises:
  an opening and closing element (17) which grants access to the fixation means (50) and containing means (100) and;
  a transportation element (18), which facilitates the transportability of the support body (10).

In the present example, the opening and closing element (17) consists of a zip, which grants access to an internal compartment, in which the fixation (50) and containing (100) means are located. Meanwhile, the transportation element (18) consists of a handle. As can be seen in FIG. 1, the device (1) is perfectly collected, being very compact and as a result, occupying very little space, with all those elements from which it is formed being housed within the support body (10) itself. This facilitates the manipulation of the device significantly, during transportation, use and collection of the same.

The fixation means (50) are those means which make it possible to fix the fastening device (1) to the chair or arm chair. The fixation means (50) comprise:
   an automatic locking retractor (51);
   a fixation strap (52) with an internal end connected to the automatic locking retractor (51) and an external end, which has a clasp mechanism (53) and;
   a retention mechanism (54), which is configured to retain the clasp mechanism (53) and which has an unclasping mechanism (55), in order to free the same.

In the present example, the clasp mechanism (53) is configured by means of a metal buckle or tongue, which is retained by a retaining mechanism (54) configured as a female connector, orientated in the opposite direction to the direction in which the fixation strap (52) is extracted. The unclasping mechanism (55) consists of a button, which makes it possible to disengage the tongue from the connector. Said button is located beyond the reach of the user or at a point which is difficult to access, in order to prevent the user from operating the same and causing unwanted release from the fastening device (1).

With the aim of providing additional fastening, the fixation means (50) additionally comprise:
   an elastic energy storage (56) arranged between the fixation strap (52) and the clasp mechanism (53) and;
   a manual tensioning element (57), which makes it possible to roll the fixation strap (52) in the automatic locking retractor (51), in order to tense the energy storage (56).

In other words, once the fixation strap (52) has been adjusted to the back of the chair, it is possible to roll a little bit more, operating on the manual tensioning element (57). In this situation, the energy storage (56) tenses but cannot free said energy because the automatic locking retractor (51) does not allow more fixation strap (52) to be extracted. The fixation strap (52) tightens with greater force to the back of the chair. This prevents the fixation strap (52) from loosening even more, thus ensuring that the device (1) has been fixed to the chair correctly. In the present example, the energy storage (56) consists of a rubber made of plastic material, which is robust enough to prevent unwanted breakages.

The containing means (100) are those means which make it possible to fasten the user in a safe and comfortable way. These means comprise:
   a first emergency locking retractor (104) orientated towards a first side (11) of the support body (10) and;
   a first containing strap (101) with an internal end, which is connected to the first automatic emergency retractor (104) and an external end, which has a first clasp element (107).

The containing means (100) additionally comprise:
   a second emergency locking retractor (105) orientated towards a second side (12) of the support body (10), opposite to the first side (11) and;
   a second containing strap (102) with an internal end, which is connected to the second emergency locking retractor (105) and an external end, which has a second clasp element (108).

The containing means (100) additionally comprise:
   a third emergency locking retractor (106) orientated towards a third side (13) of the support body (10) and;
   a third containing strap (103) with an internal end which is connected to the third emergency locking reactor (106) and an external end which has a third clasp element (109) to clasp the containing pad (120).

The third side (13) of the support body (10) corresponds to a lower side of the same, arranged between the first (11) and second side (12), in such a way that the third containing strap (103) is orientated towards the seat of the chair or arm chair. The third containing strap (103) is generally longer than the first (101) or second (102) containing strap, given that it is provided with a greater usage pathway.

For users with more critical mobility conditions, it may be necessary to impede any kind of movement. For this reason, each emergency locking reactor (104, 105, 106) comprises a manual locker (114, 115, 116) configured to impede the free movement of the person fastened to said chair or arm chair. Said manual locker (114, 115, 116) disables the smooth removal of the containing straps (101, 102, 103) once they have been adjusted to the user.

Figure 3:
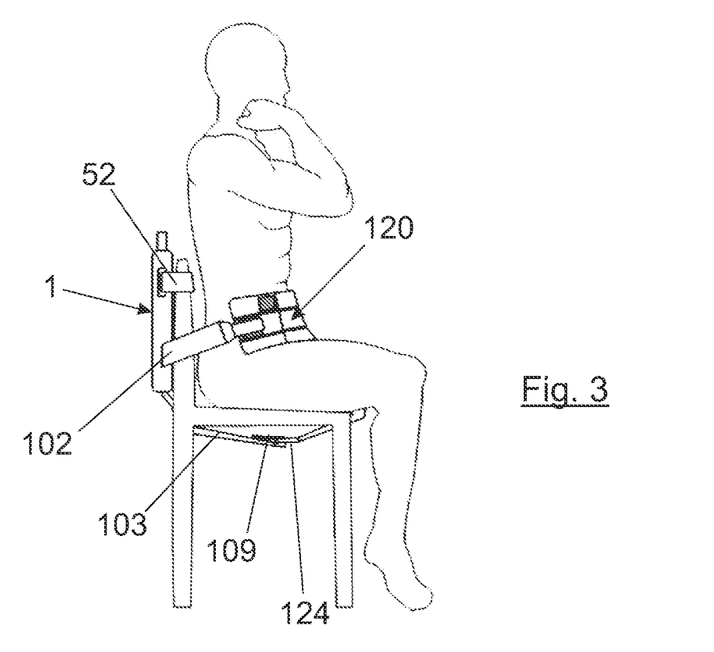
FIG. 3 is a first profile view of the fastening device, object of the present invention, in the position it adopts when in use.
Figure 4:
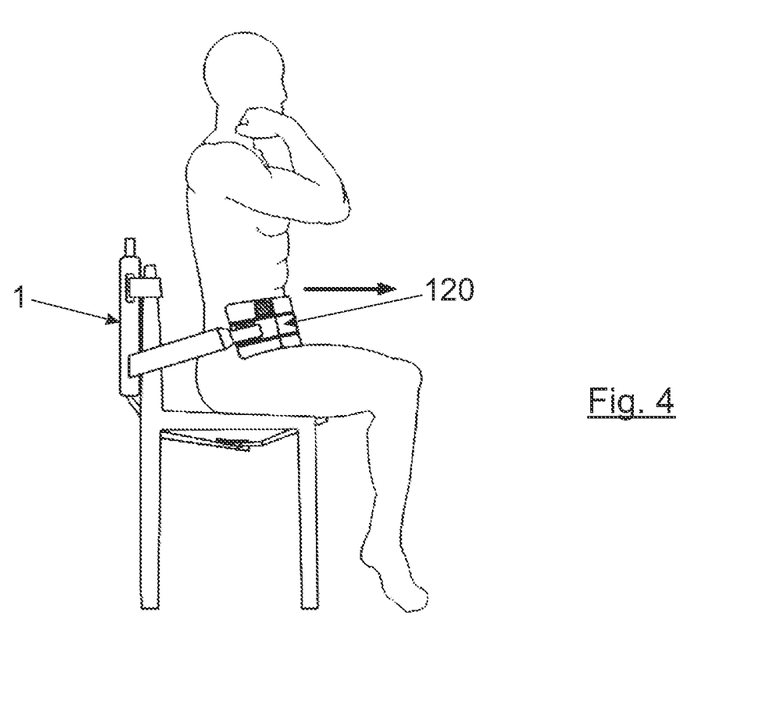
FIG. 4 is a second profile view of the fastening device, object of the present invention, in the position it adopts when in use.

FIGS. 3 and 4 are respective first and second profile views of the fastening device, object of the present invention, in the position it adopts when in use. The thoracic area is not fastened. As can be seen, the fastening device (1) is configured in order to facilitate free movement, reflected by the arrow, of the person fastened to said chair.

Figure 5A:
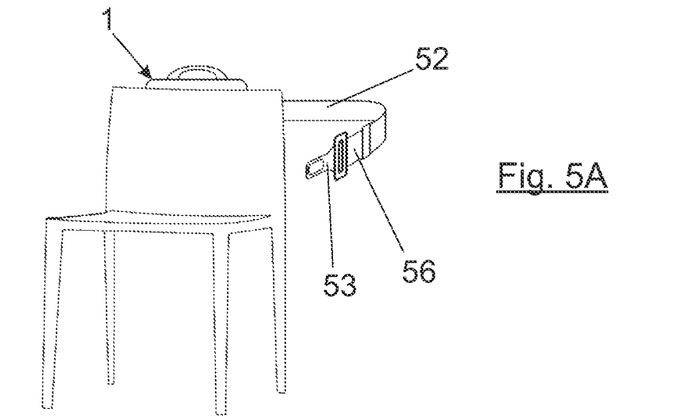
FIGS. 5A, 5B and 5C are a series of perspective representations of the stages required in order to fix the fastening device to the back of a chair.
Figure 5B:
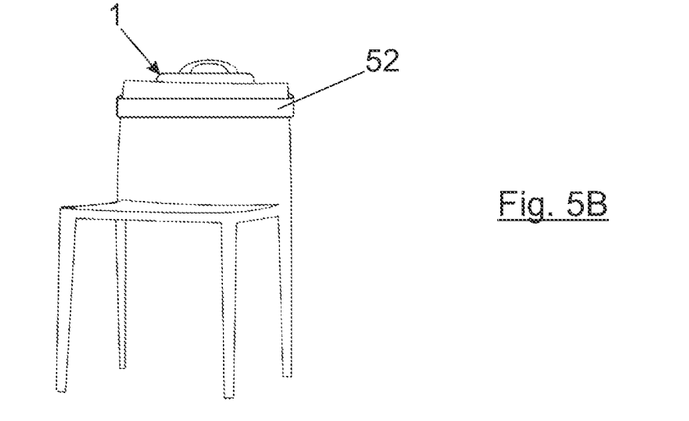
Figure 5C:
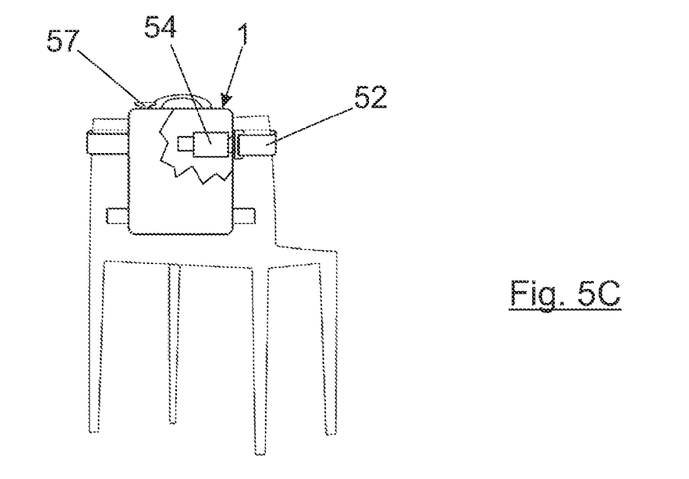

FIGS. 5A, 5B and 5C are a sequence of perspective representations which demonstrate the stages required in order to fix the fastening device to the back of a chair, according to a normal operational method. In the first instance, the device (1) is arranged in the rear portion of the back of the chair. The necessary fixation strap (52) is subsequently extracted and the locking mechanism is activated, which prevents more strap (52) from being removed Immediately after this, the clasp mechanism (53) is connected to the retaining mechanism (54) and the fixation strap (52) is loosened, in order for it to be collected automatically by means of an internal spring, until it is adjusted to the back of the chair. At this stage, it is not possible to extract any more fixation strap (52), given that the locking mechanism has been activated. This prevents the same from becoming loose and as a result, prevents the device (1) from becoming detached. In order to provide additional fastening, a little bit more of the fixation strap (52) may be rolled, acting on the manual tensioning element (57). When the clasp mechanism (53) is freed from the retaining mechanism (54), the fixation strap (52) is collected completely on the automatic locking retractor (51), which is when the locking mechanism is deactivated, once again allowing the strap (52) to be removed.

Figure 6:
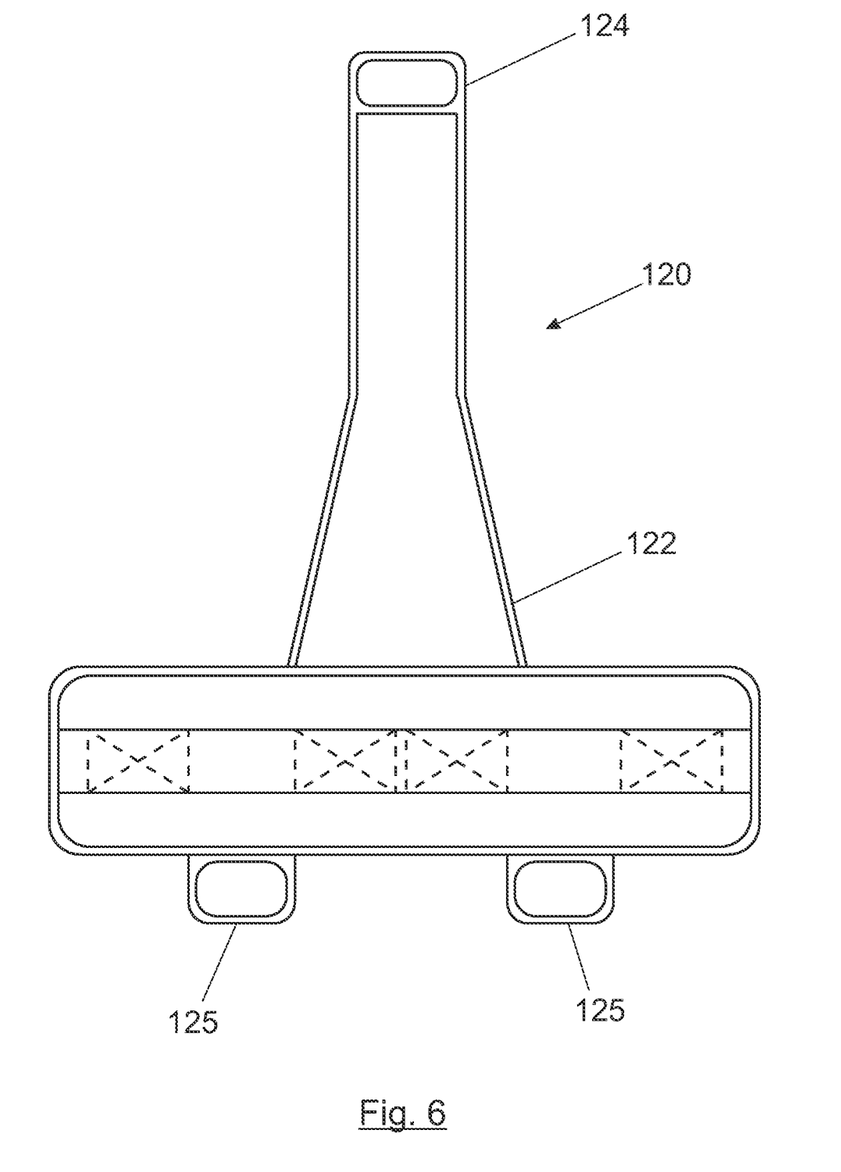
FIG. 6 is a plan view of the internal face of the containing pad.

FIG. 6 is a plan view of the internal face of the containing pad (120). As can be seen, the containing means (100) comprise a flexible containing pad (120), which has:
   an abdominal piece (121) and;
   an inguinal piece (122), which extends perpendicularly from said abdominal piece (121).

Figure 7A:
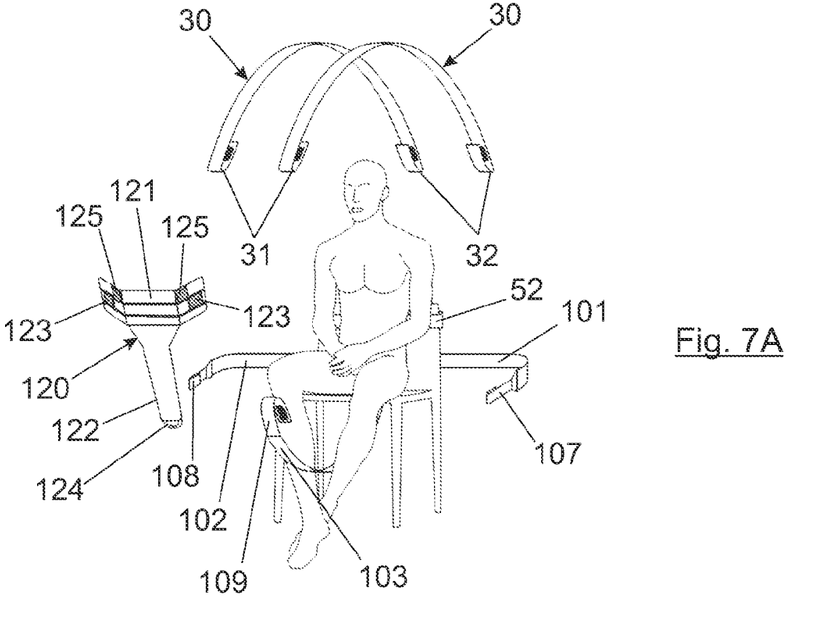
FIGS. 7A and 7B are respective representations, one providing a frontal perspective view and the other a rear perspective view, with a breakdown of the containing means.
Figure 7B:
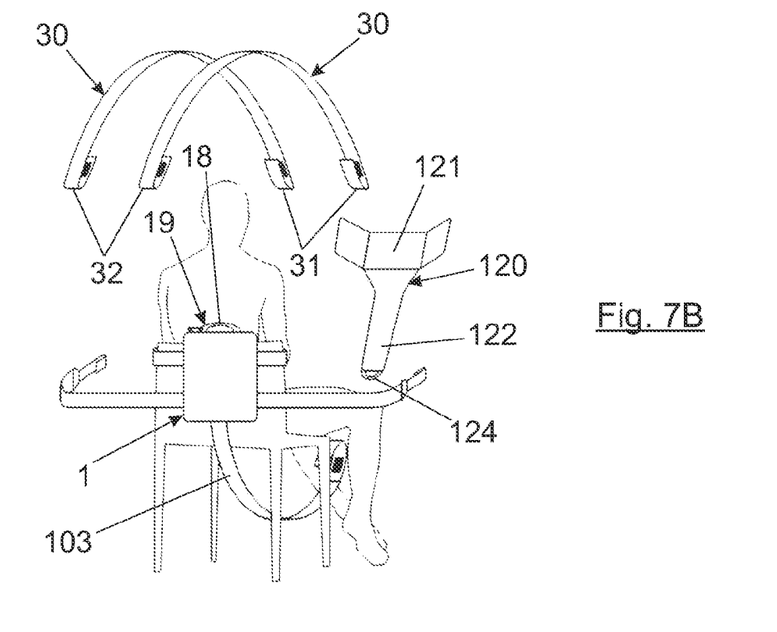

FIGS. 7A and 7B are respective representations, one being a frontal perspective view and the other a rear perspective view, with a breakdown of the containing means (100). As can be observed when looking at these figures, the abdominal piece (121) comprises two lateral anchoring elements (123), configured to anchor the first (107) and second clasp elements (108). The side anchoring elements (123) serve as pockets, made up on the pad itself (120), whilst the clasp elements (107, 108) serve as a hook.

The inguinal piece (122) comprises a lower anchoring element (124), configured to anchor the third clasp element (109). The lower anchoring element (124) is formed by a hoop made of textile material, also made up on the pad itself (120), in which the third clasp element (109) can be joined, which in turn has a quick opening and closing system of the velcro® variety.

The fastening device (1) additionally comprises two thoracic fastening straps (30), configured to be joined to the containing pad (120) and to the support body (10). Therefore, the abdominal piece (121) comprises at least one upper anchoring element (125), configured to anchor a first end (31) of the fastening strap (30), whilst the support body (10) comprises at least one external anchoring element (19), configured to anchor a second end (32) of the fastening strap (30). In the present example, the transportation element (18) of the support body (10) itself is benefitted from as an external anchoring element (19).

The upper anchoring elements (125) are formed by bands of textile material made up on the pad itself (120), which work alongside the first ends (31) of the fastening straps (30). Alternatively, they may be configured by means of hoops or rings, which facilitate the first ends (31) being tied, as in the particular case represented in FIG. 6. In turn, both the first end (31) and the second end (32) of the fastening strap (30) are configured by quick opening and closing systems of the Velcro® variety, which may be joined and/or tied to the bands of the pad (120) and to the external anchoring elements (19) of the support body (10).

Figure 7C:
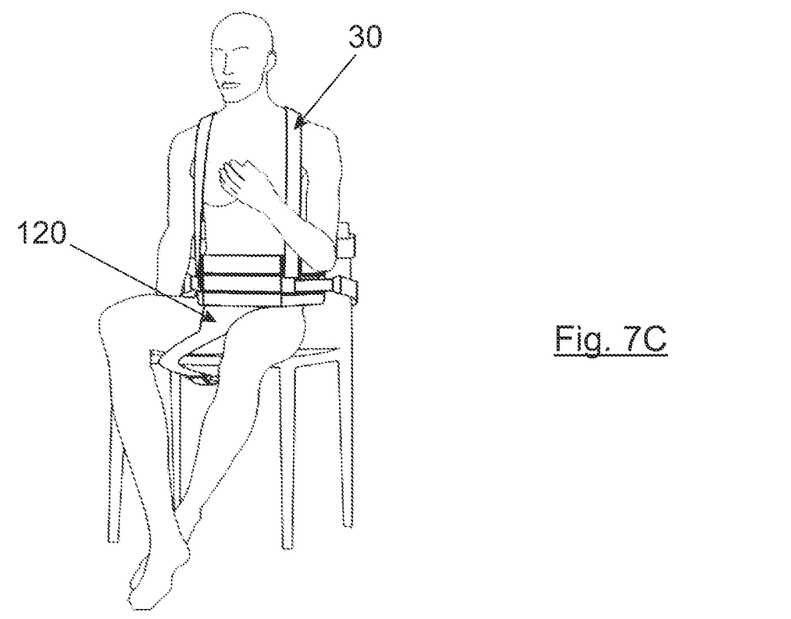
FIGS. 7C and 7D are respective representations, one providing a frontal perspective view and the other a rear perspective view, with the containing means fastening the user.
Figure 7D:
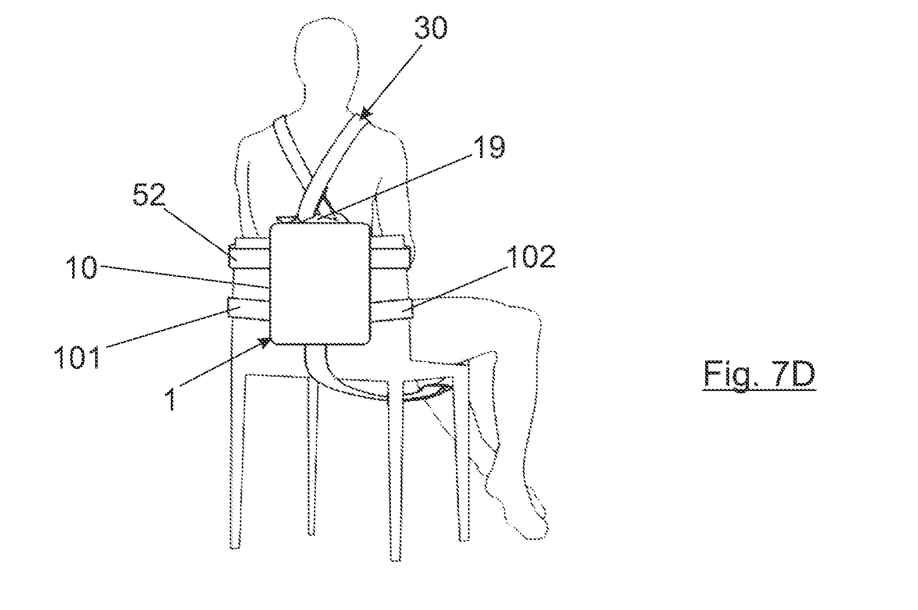

FIGS. 7C and 7D are respective representations, one being a frontal perspective view and the other a rear perspective view, with containing means fastening the user. As can be seen, the user remains seated on the chair, fastened at their abdominal, inguinal and thoracic areas, having free and controlled movement of these areas, whilst also being protected against eventual falls.

Figure 8:
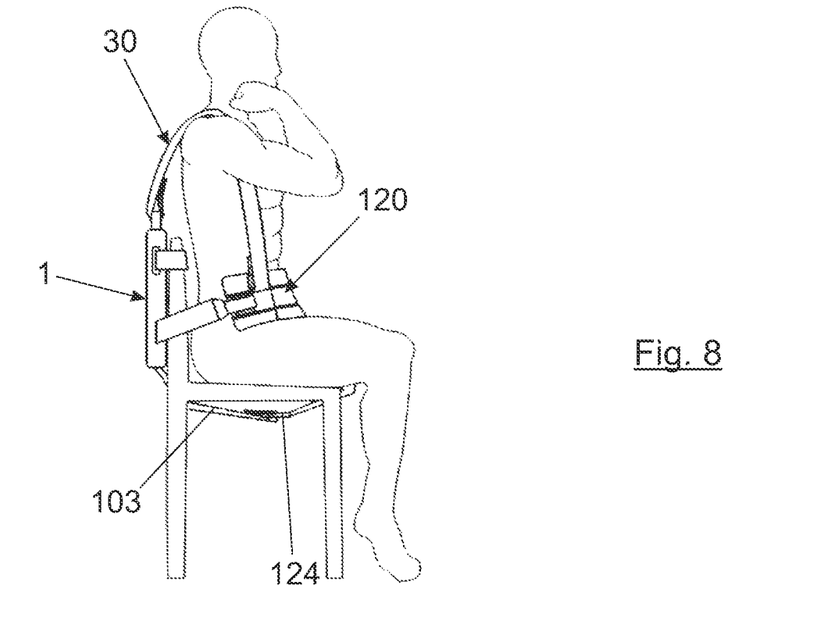
FIG. 8 is a third profile view of the fastening device, object of the present invention, in the position it adopts when in use.
Figure 9:
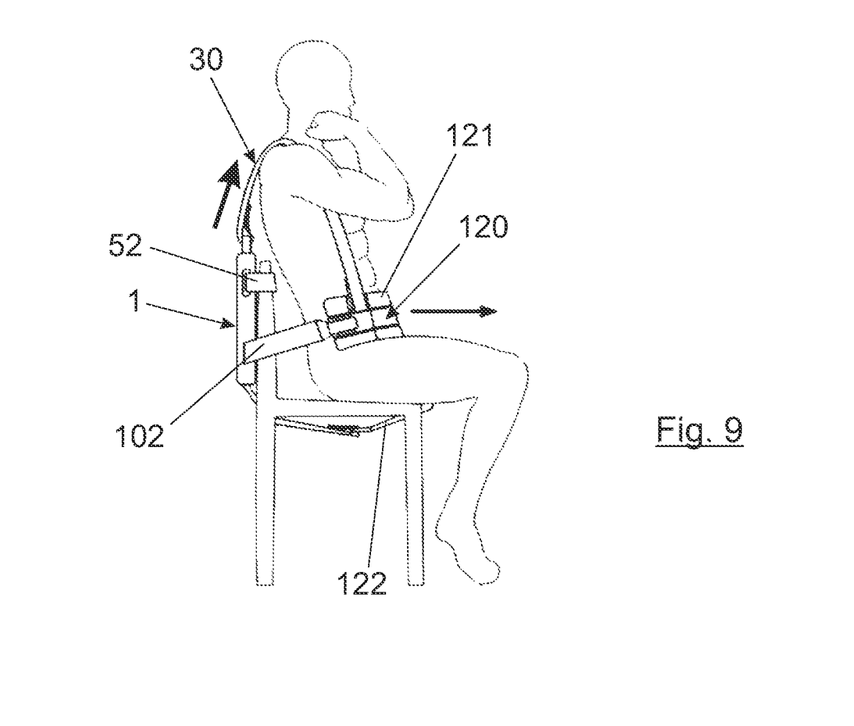
FIG. 9 is a fourth profile view of the fastening device, object of the present invention, in the position it adopts when in use.

FIGS. 8 and 9 are respective profile views of a third and fourth fastening device, object of the present invention, in the position it adopts when in use. The thoracic area is fastened by fastening straps (30). As can be seen, the fastening device (1) is configured in order to facilitate the free movement, reflected by the arrow, of the person fastened to said chair.

The invention claimed is:

1. A fastening device for people with reduced mobility conditions, of the variety employed in chairs or arm chairs in domestic, geriatric, care or hospital environments, comprising fixation means which can be adapted to the back of the chair or arm chair, containing means provided with a containing strap to contain a person to be fastened, and a portable support body in which said fixation means and containing means are arranged, wherein the containing strap is connected to an emergency locking retractor, provided with an inertial locking mechanism, which is configured to facilitate a smooth removal of the containing strap, once the same has been adjusted to the person to be fastened, and at the same time instantly locking said removal when a brusque movement from the person to be fastened is detected, the support body comprising an opening and closing element which grants access to the fixation means and containing means, and a transportation element, which makes the support body portable, the fixation means comprising an automatic locking retractor, a fixation strap with an internal end connected to the automatic locking retractor and with an external end which has a clasp mechanism, and a retaining mechanism, which is configured to retain the clasp mechanism and which has an unclasping mechanism, in order to free the same, and the automatic locking retractor being configured to block the removal of the fixation strap, once it has been adjusted to the back of the chair or arm chair.

2. The fastening device for people with reduced mobility conditions, according to claim 1, wherein the support body comprises:

a support base, arranged inside said support body, upon which the fixation means and containing means are supported; and a plurality of openings which extend said fixation means and said containing means and facilitate the manipulation of the same.

3. The fastening device for people with reduced mobility conditions according to claim 1, wherein the fixation means additionally comprise:

an elastic energy storage arranged between the fixation strap and the clasp mechanism; and a manual tensioning element, which makes it possible to roll the fixation strap in the automatic locking retractor in order to tense the energy storage.

4. The fastening device for people with reduced mobility conditions according to claim 1, wherein the emergency locking retractor is a first emergency locking retractor orientated towards a first side of the support body; and the containing strap is a first containing strap with an internal end, which is connected to the first emergency locking retractor and with an external end which has a first clasp element.

5. The fastening device for people with reduced mobility conditions according to claim 4, wherein the containing means further comprise:

a second emergency locking retractor orientated towards a second side of the support body opposite the first side; and a second containing strap with an internal end which is connected to the second emergency locking retractor and with an external end which has a second clasp element.

6. The fastening device for people with reduced mobility conditions, according to claim 5, wherein the containing means further comprise:

a third emergency locking retractor orientated towards a third side of the support body; and a third containing strap with an internal end which is connected to the third emergency locking retractor and an external end which has a third clasp element.

7. The fastening device for people with reduced mobility conditions according to claim 6, wherein the containing means comprise a flexible containing pad which has:

an abdominal piece; and an inguinal piece which extends perpendicularly from said abdominal piece, wherein the inguinal piece comprises at least one lower anchoring element, configured to anchor the third clasp element.

8. The fastening device for people with reduced mobility conditions according to claim 5, wherein the containing means comprise a flexible containing pad which has:

an abdominal piece; and an inguinal piece which extends perpendicularly from said abdominal piece, wherein the abdominal piece comprises at least one lateral anchoring element configured to anchor the first clasp element or the second clasp element.

9. The fastening device for people with reduced mobility conditions according to claim 1, wherein the containing means comprise a flexible containing pad which has:

an abdominal piece; and an inguinal piece which extends perpendicularly from said abdominal piece.

10. The fastening device for people with reduced mobility conditions according to claim 9, further comprising at least one thoracic fastening strap configured to be joined to the containing pad and to the support body.

11. The fastening device for people with reduced mobility conditions according to claim 10, wherein the abdominal piece comprises at least one upper anchorage element configured to anchor a first end of the fastening strap.

12. The fastening device for people with reduced mobility conditions according to claim 10, wherein the support body comprises at least one external anchoring element configured to anchor an end of the fastening strap.

13. The fastening device for people with reduced mobility conditions according to claim 1, wherein the at least one emergency locking retractor comprises a manual locker configured to impede free movement of the person fastened to said chair or arm chair.

\* \* \* \* \*